United States Patent [19]

Witbeck

[11] Patent Number: 5,508,027

[45] Date of Patent: Apr. 16, 1996

[54] PROCESS AND COMPOSITION FOR STRENGTHENING NAILS

[76] Inventor: Mickey Witbeck, 1139 Battery La., Nashville, Tenn. 37220

[21] Appl. No.: 646,684

[22] Filed: Jan. 28, 1991

[51] Int. Cl.$^6$ ............................................. A61K 7/043
[52] U.S. Cl. ................................................. 424/61; 424/401
[58] Field of Search ................... 424/61, 81; 524/238, 524/558

[56] References Cited

U.S. PATENT DOCUMENTS

| | | | |
|---|---|---|---|
| 4,071,645 | 1/1978 | Kahn | 524/238 |
| 4,158,053 | 6/1979 | Greone et al. | 424/61 |
| 4,260,701 | 4/1981 | Lee, Jr. | 424/61 X |
| 4,766,005 | 8/1988 | Montgomery et al. | 424/61 X |
| 4,897,261 | 1/1990 | Yamazaki et al. | 424/61 |
| 4,916,178 | 4/1990 | Amati et al. | 524/558 |
| 4,919,920 | 4/1990 | Devos | 424/61 |
| 5,120,529 | 6/1992 | Koch et al. | 424/61 |

*Primary Examiner*—Thurman K. Page
*Assistant Examiner*—J. Venkat
*Attorney, Agent, or Firm*—Kane, Dalsimer, Sullivan, Kurucz, Levy, Eisele and Richard

[57] ABSTRACT

Nails (ungues) are strengthened by periodic applications of films of an acrylic polymer to the nail body, over a period of time.

8 Claims, No Drawings

PROCESS AND COMPOSITION FOR STRENGTHENING NAILS

BACKGROUND OF THE INVENTION

1. Field of the Invention

The invention relates to a process and composition for improving the strength of nails (ungues) of animals, including humans. The nails (ungues) are composed of clear, horny cells of the epidermis, joined so as to form a solid, continuous plate upon the dorsal surface of the terminal phalanges. Each nail is closely adherent to the underlying corium, which is modified to form what is called the bed, or matrix. The body of the nail is the part that shows. The hidden part, in the nail groove, is called the root.

The nails grow in length by multiplication of the soft cells in the stratum germinativum at the root. The cells are transformed into hard, dry scales, which unite to form a solid plate; and the nail, constantly receiving additions, slides forward over its bed and projects beyond the end of the finger. When a nail is thrown off by suppuration or town off by violence, a new one will grow in its placed provided any of the cells of the stratum germinativum are left.

On occasion and in some individuals, the hard plate forming the nail body is brittle or tears readily. Optimum hardness and strength are not achieved. Also, certain individuals are prone to chew (masticate) on the nail body removing portions thereof. This removal is facilitated by a relatively low body strength.

Employing the process and the compositions of the invention, the strength of nails is improved. Nails obtain an enhanced resistance to splitting, peeling, chipping and breaking. Associated cuticles and ridges become smoother. The nails become more resistant to the usual effects of chewing and are harder to chew.

SUMMARY OF THE INVENTION

The invention comprises a process for improving the strength of an unguis, which comprises;

applying to the unguis body a film of a synthetic gum selected from the group consisting of acrylic polymers; and maintaining a film of said gum on the body as it grows in length.

The invention also comprises an aqueous composition containing as the active ingredient a synthetic gum selected from the group consisting of acrylic polymers. The aqueous compositions are useful in the process of the invention.

The term "gum" as used herein means a material that can be dissolved or dispersed in water to give viscous solutions or dispersions.

DETAILED DESCRIPTION OF THE PREFERRED EMBODIMENTS OF THE INVENTION

Synthetic gums selected from acrylic polymers are well know resins including polyacrylic acid and polyacrylamide. Advantageously the acrylic polymer selected will have a weight average molecular weight ($M_w$) of more than 2000, preferably at least 1,000,000 and most preferably within the range of from 3,000,000 to 5,500,000 Daltons (determined by gel permeation chromatography).

Preferably the resin employed is the alkali metal salt, for example the sodium or potassium salt. Most preferably, the resin employed is the alkali metal salt of polyacrylic acid such as poly (acrylic acid), sodium salt. Poly (acrylic acid), sodium salt is a commercially available resin, and can be obtained in aqueous solutions thereof.

Films of the acrylic polymer may be applied to the nail body from coatings of aqueous solutions and dispersions. Upon drying an applied coating the resin forms a continuous film on the surface of the nail body.

The film of the gum resin may be maintained on the body of the nail as it grows in length by periodic re-application of the aqueous coatings as the nail grows. Although a single application of a polyacrylic film will strengthen a nail, advantageously, coatings of the film are applied from 1 to 5 times a day to 1 to 3 times a week to maintain the film presence, preferably in the evening before retiring to sleep. The process is most beneficial when repeated applications over a period of at least about 1 month are made.

Aqueous film forming resin compositions employed in the process of the invention are advantageously compositions of the invention. These compositions include the synthetic gum resin in a proportion within the range of from about 0.5 to about 50 percent by weight of the water carrier.

The compositions of the invention may also contain sufficient of an alkali metal base, when required, to maintain a near neutral or slightly basic pH in the aqueous compositions. For example, a pH of from about 6.5 to about 8.0 is advantageous. Representative of alkali metal bases are sodium hydroxide, potassium hydroxide and preferably ammonium hydroxide.

Commercially available forms of poly (acrylic acids), sodium salt generally contain residual carboxyl groups (circa 10 percent residual groups). The resins, as found in the compositions of the invention are preferably further neutralized by the added presence of sodium hydroxide.

Preferred compositions of the invention include a volatile fragrance. Volatile fragrances employed in the compositions of the invention include natural essential oils and synthetic perfumes, and blends thereof.

The term "perfume" as used herein refers to odoriferous materials which are able to provide a pleasing fragrance and encompasses conventional materials commonly used to counteract a malodor in such compositions and/or provide a pleasing fragrance thereto. The perfumes may be in the liquid state at ambient temperature. Included among the perfumes contemplated for use herein are materials such as aldehydes, ketones, esters and the like which are conventionally employed to impart a pleasing fragrance to liquid compositions. Naturally occurring plant and animal oils are also commonly used as components of perfumes. Accordingly, the perfumes useful for the present invention may have relatively simple compositions or may comprise complex mixtures of natural and synthetic chemical components, all of which are intended to provide a pleasant odor or fragrance when mixed in water.

The fragrance is preferably substantially soluble in water. The fragrance may be added to the compositions of the invention in a fragrance emitting proportion. A fragrance emitting proportion is generally within the range of from 0.1 to 10 percent by weight of the total composition.

Representative of fragrance are: natural essential oils such as lemon oil, mandarin oil, clove leaf oil, petitgrain oil, cedar wood oil patchouli oil, lavadin oil, neroli oil, ylang oil, rose absolute or jasmin absolute; natural resins such as labdanum resin or olibanum resin; single perfumery chemicals which may be isolated from natrual sources or manufactured synthetically, as for example alcohols such as geraniol, nerol, citronellol, linalool, tetrahydrogeraniol, betaphenylethyl alcohol, methyl phenyl carbinol, dimethyl benzyl carbinol, methol or cedrol; acetates and other esters derived from such alcohols-aldehydes such as citral, citronellal, hydroxycitronellal, lauric aldehydes such as citral, citronellal, hydroxycitronellal, lauric aldehyde, undecylenic aldehyde, cinnamaldehyde, amyl cinnamic aldehyde, vanillin or heliotropin; acetals derived from such aldehydes; ketones such as methyl hexyl ketone, the ionones and the methylionones; phenolic compounds such as eugenol and isoeugenol; synthetic musks such as musk xylene, musk ketone and ethylene brassylate and the like.

The compositions of the invention are prepared by a homogeneous mixing of the desired ingredients in water.

The following example describes the manner and process of making and using the invention and sets forth the best mode contemplated by the inventor but are not to be construed as limiting.

EXAMPLE

The following ingredients were mixed together to obtain an aqueous solution:

| Ingredient | Weight |
| --- | --- |
| polyacrylic acid | 4 lbs. |
| sodium hydroxide | 0.3 lbs. |
| ammonium hydroxide | 0.5 lbs. |
| fragrance oil | 32.3 gms. |
| deionized water | 150 lbs. |

When coated on the body of fingernails (human) 3 times a week for a period of 1 month, the nails showed improvements in strength as exhibited by a resistance to splitting, peeling, chipping and breaking.

What is claimed is:

1. A process for improving the strength of an unguis, which comprises;

applying to the unguis body a film consisting of a poly-(acrylic acid) sodium salt; and maintaining said film on the body as it grows in length.

2. The process of claim 1 wherein application is from an aqueous solution or dispersion of the poly (acrylic acid) sodium salt.

3. An aqueous solution with pH which is neutral or basic, which consists of;

poly(acrylic acid) sodium salt;

water;

a perfume fragrance; and a pH adjusting agent.

4. The process of claim 1 wherein maintenance is carried out by repeating the application.

5. The process of claim 4 wherein applications are 1 to 5 times a day to 1 to 3 times a week for at least a month.

6. The process of claim 1 wherein the unguis is a human unguis.

7. The process of claim 1 wherein application of the film comprises coating the unguis with an aqueous solution or dispersion of the polymer.

8. The process of claim 7 wherein the solution consists essentially of;

poly (acrylic acid) sodium salt;

water;

a perfume fragrance; and sufficient of a pH adjusting agent to obtain a solution with a pH of from about 6.5 to about 8.0.

* * * * *